(12) United States Patent
Staecker (10) Patent No.: US 7,387,614 B2
(45) Date of Patent: Jun. 17, 2008

(54) DRUG DELIVERY TO THE INNER EAR AND METHODS OF USING SAME

(75) Inventor: Hinrich Staecker, Reisterstown, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 279 days.

(21) Appl. No.: 10/895,418

(22) Filed: Jul. 21, 2004

(65) Prior Publication Data

US 2005/0095270 A1 May 5, 2005

Related U.S. Application Data (60) Provisional application No. 60/489,229, filed on Jul. 21, 2003, provisional application No. 60/498,722, filed on Aug. 28, 2003.

(51) Int. Cl.
*A61B 16/00* (2006.01)
*A61B 6/00* (2006.01)
*A61F 11/00* (2006.01)
*A61K 38/00* (2006.01)

(52) U.S. Cl. .......................... 604/19; 514/2; 604/103.02
(58) Field of Classification Search .................. 514/2, 514/44; 424/278.1
See application file for complete search history.

(56) References Cited

U.S. PATENT DOCUMENTS

| 5,168,062 | A | | 12/1992 | Stinski |
| 5,385,839 | A | | 1/1995 | Stinski |
| 5,474,529 | A | * | 12/1995 | Arenberg ..................... 604/21 |
| 6,177,259 | B1 | | 1/2001 | Yuan et al. |
| 6,228,603 | B1 | | 5/2001 | Reed et al. |
| 6,440,102 | B1 | | 8/2002 | Asenberg et al. |
| 2002/0106631 | A1 | * | 8/2002 | Alnemri ......................... 435/4 |

OTHER PUBLICATIONS

Procedures (2006) Network of Florida Otolaryngologists, http://www.floridaent.org/nfent-ear.htm, pp. 1-2.*
Stapedectomy (2006) Answers.com, http://www.answer.com/topic/stapedectomy, pp. 1-4.*
Shimizu et al. (2003) Calpain and caspase inhibitors protect vestibular sensory cells from gentamincin ototoxicity. Acta Otolaryngol. vol. 123, No. 4, pp. 459-465.*
Water et al. (1999) Gene therapy in the inner ear, Ann. New York Acad. Sci., vol. 884, issue 1, pp. 345-360.*
Mizuguchi et al. (1999) A simple method for constructing E1- and E1/E4-deleted recombinant adenoviral vectors. Hum. Gene Ther. vol. 10, No. 12, pp. 2013-2017.*
Raphael et al. Neurosci. Lett. 1996; 207:137-141.
Smith, A.E., Ann. Rev. Microbiol. 1995; 49:807-39.
Jero, J. Et al., Hear. Res. 2001; 151:106-114.
Kawamoto, H. Et al., Mol Ther. 2001; Dec: 4(6):575-585.
Staecker, H., et al., Acta Otolaryngol. 2001; 121:157-163.
Hodges, A.V., et al., Am. J. Otol. 1997; 8:179-183.
Praetorius, M., et al., J. ORL 2003;65:211-214.
Luebke A.E., et al., Hum. Gene Ther., 2001; 12:773-781.

* cited by examiner

*Primary Examiner*—Karen Cochrane
*Assistant Examiner*—Samuel W. Liu
(74) *Attorney, Agent, or Firm*—Jacobson Holman PLLC (57) ABSTRACT

The inventors have demonstrated that they can deliver therapeutic compositions to the inner ear of mammals via a variety of routes including the round window membrane, the semicircular canals, via cochleostomy and through the stapes footplate. Using pancaspase inhibitors, the inventors have shown that relatively large volumes of compositions can be injected with little to no hearing loss.

4 Claims, 6 Drawing Sheets

DRUG DELIVERY TO THE INNER EAR AND METHODS OF USING SAME

This is a complete application claiming benefit of provisional 60/489,229 filed Jul. 21, 2003 and provisional 60/498,722 filed Aug. 28, 2003.

FIELD OF INVENTION

The present invention relates generally to the delivery of therapeutic agents to the inner ear of a mammal. More specifically, the present invention relates to the delivery of pharmaceutical compositions, molecular agents or proteins of interest to the inner ear and their use in allowing relatively large volumes of therapeutics to be administered into the inner ear without substantial loss of inner ear function.

Introduction

The inner ear of mammals and humans consists of two separate organ systems responsible for the sensation of hearing and balance. Diagnosis and treatment of inner ear disorders to date is largely dependent on indirect methods of examination. Treatment of inner ear disorders is presently also limited by the potential damage that can be caused by inserting instrumentation into the ear. As such, the current challenges to inner ear medicine include limiting the potential damage to functional portions of the inner ear during procedures such as cochlear implantation.

Over the last 5 years, there have been numerous publications describing gene delivery to the inner ear. Several different vectors have been studied and shown to successfully transfer functional genes into the mammalian auditory system. The inner ear is a particularly attractive target for gene therapy because vectors can be easily delivered to the localized structure of the inner ear.

Adenoviruses have been shown to transfer functional marker genes such as β-galactosidase (βgal) and green fluorescent protein (GFP), as well as genes which can alter the biology of the inner ear, such as glial derived neurotrophic factor (GDNF) to the auditory system (Raphael et al. Neurosci. Lett. 200; 207: 137-41). The most commonly used adenoviral vectors are E1/E3 deletion mutants that allow the insertion of up to 10 kb of foreign DNA into the viral vector genome. Expression of transfected genes in vivo from adenoviral vectors has been demonstrated for time periods ranging from weeks in adults, to much longer in neonates and in culture. Loss of gene expression after these time periods is associated with host immune responses against virally infected cells, which has historically limited adenoviral vector use for long-term expression (Smith, A. E., Ann. Rev. Microbiol. 1995; 49:807-39).

For example, Raphael et al. have demonstrated transfer and expression of the bacterial lac Z gene within guinea pig cochlea using replication deficient adenovirus (Raphael et al., supra). Many studies have used guinea pigs with delivery to the cochlear perilymphatic space as a model due to ease of surgical access.

Another mammalian model is the mouse. Mice have the advantage of having better-defined genetics and thus knockout mice could potentially be used as models for human disease so that a variety of inner ear gene therapy strategies could be tested. The disadvantages of the mouse model are difficulty of surgical access and the loss of hearing that is frequently encountered when violating the mouse inner ear (Jero, J. et al., Hear. Res. 2001; 151:106-114). However, injection of viral vector into the semicircular canals has been used to deliver adenovirus to the mouse inner ear without hearing loss, although this did not result in widespread expression and distribution of transgene product throughout the inner ear (Kawamoto, K. et al., Mol. Ther. 2001; Dec. 4(6):575-585). Basal turn approaches have also been described in the art (Kawamoto et al.).

Many of the above experiments have used an osmotic minipump to deliver the vector. Id. Although use of this device appears to be fairly atraumatic, it can be difficult to exactly control the quantity of total vector delivered. To develop a gene delivery approach to inner ear disease and to maintain safety, the relationships between total dose of vector delivered and the resulting distribution of gene expression need to be established.

For the mouse, the vector could be delivered via the semicircular canal; or alternatively, vector can be delivered through the round window membrane although it has been considered technically difficult, and has a high likelihood of damaging hearing, but it ultimately provides a wide distribution of vector to the inner ear. It is not clear how traumatic the latter approach is in terms of hearing (Staecker, H., et al., Acta Otolaryngol. 2001; 121:157-163). There is also precedence for applying this approach in humans where procedures like puncturing the round window vs. direct injection, as well as differences in distribution of tissue receptors, can influence the ability to deliver genes to various cell types within the inner ear (Schuknecht H. F., et al., Laryngoscope 1982; 92(8 Pt. 1):853-858; Hodges, A. V., et al., Am. J. Otol. 1997; 8:179-183).

Previously, several different pathways or routes of administration have been used to access the inner ear including, but not limited to the following detailed below.

The first route of administration is delivery to the round window membrane via various techniques. This technique relies on diffusion of molecules through the round window membrane, thus some large molecules are unable to pass. Additionally, definitive dose response curves cannot be developed for a drug through this approach as a result of the difficulty in quantifying the diffusion kinetics of the membrane. Therapeutic compounds can also be administered by injection through the round window membrane. This technique is possible in humans, based on the cochleosacculotomy operation, and recent data on hearing preservation in cochlear implant patients. This latter approach delivers first to the basal turn of the cochlea and has a much higher published rate of hearing loss (based on cochleosacculotomy data). See Schuknecht H. F., supra.

The second route of administration is injection into the semicircular canals. Based on surgical experience, it is possible to open the semicircular canals and not lose hearing. This requires a major operative intervention and has higher risks of hearing loss and balance dysfunction than an intervention at the stapes footplate.

A third route of administration is injection into the endolymphatic sac. There is little available data on distribution of drug delivery through the inner ear. This technique would also require a significant operative intervention.

Further background on delivery of therapeutic compounds to the inner ear can be found in U.S. Pat. No. 6,440,102 and is incorporated by reference herein as if fully set forth in its entirety.

Until the work of the present inventors described herein, there was no consistent means of delivering a volume of drug or therapeutic into the cochlea of a mammal without risking significant hearing loss.

SUMMARY OF THE INVENTION

The present inventors have conducted studies where E1/E3 and E1/E3/E4 deleted adenoviral vectors (AD11D) carrying the green fluorescent protein (GFP) gene were injected into the round window, the basal turn of the cochlea (via a cochleostomy) or into the superior semicircular canal. Hearing was then tested 24 hours after viral gene transfer. Surprisingly, large vector titers in small volumes of fluid were well tolerated with the round window approach resulting in complete hearing preservation with transfer of GFP to hair cells and spiral ganglion cells. Injection of comparable doses of vector into a basal turn cochleostomy resulted in high-frequency hearing loss.

Most notably, when the technique was coupled with the addition of a pancaspase inhibitor, the combination protected hearing when larger volumes of fluid (e.g. greater than about 10% of the total inner ear volume) were administered to the inner ear. The inventors have published some of this work recently (Praetorius, M., et al., J. ORL 2003;65:211-214).

Research completed by the inventors and disclosed herein demonstrates that use of cell death inhibitors such as the caspase inhibitor zVAD-FMK (N-benzyloxycarbonyl-Val-Ala-Asp-fluoromethylketone) can prevent inner ear trauma caused by hydraulic/mechanical injury to the inner ear. Id.

Further research disclosed herein shows that the inventors were able to inject E1/E3/E4 deleted adenoviral vectors (AD11D) carrying the green fluorescent protein (GFP) gene were injected into a hole drilled into the stapes footplate with a laser, without any loss of hearing. Distribution of GFP activity was seen in the spiral ganglion, vestibular ganglion and isolated sections of the sensory epithelium, demonstrating that this approach is also effective in an animal model.

As such, it is an object of the present invention to provide a method for delivery of drugs or therapeutics into the inner ear of a mammal without significant loss of hearing.

It is a further object of this invention to treat the inner ear prophylactically to protect the inner ear from anoxia/sound trauma.

It is yet another object of the present invention to treat the inner ear of a mammal to protect the inner ear when the inner ear is opened and manipulated.

It is also another object of the present invention to prevent hearing loss in a mammal by pretreating the inner ear with alternate apoptosis inhibitors such as inhibitors of c-jun kinase, molecules altering the bcl-2/bax ratio or inhibitors of specific caspases or calpains.

It is yet another object of the present invention that the compositions and methods of use disclosed herein can be used to aid in cochlear implantation with hearing preservation by preventing damage to the inner ear during cochlear implantation.

It is a still further object of the present invention that the techniques disclosed can also be used in skull base surgery when the inner ear is opened to provide more extensive surgical approaches to the cranial vault.

It is another object of the present invention to use the technology disclosed herein to include infusion of apoptosis inhibitors during endoscopy of the inner ear so as to protect against potential hearing loss.

BRIEF DESCRIPTION OF THE DRAWINGS

FIGS. 2A-2E are fluorescent micrographs of GFP expression after delivery by an E4-deleted adenovector. GFP expression can be seen in the stria vascularis (2A), the inner hair cell (2B), the outer hair cells (2C), supporting cells and hair cells in the cristae (2D), the spiral ganglion (2E) and in supporting cells and hair cells of the macular organs.

FIGS. 3A and 3D represent untreated controls. FIGS. 3B and 3E show an organ of Corti treated with the chemotherapeutic agent cisplatin. There is loss of cells and loss of mitochondrial function. FIGS. 3C and 3F show an organ of Corti pretreated with an adenovector with bcl2 expression followed by cisplatin treatment. The hair cells in 3C and 3F remain intact demonstrating the potential to protect from chemotherapy induced mitochondrial dysfunction and cell death.

FIGS. 4A-4D are photographs of the approach to the mouse inner ear. The mouse bulla is opened (4A), and the cochlea is exposed to allow creation of a cochleostomy (4B) or stapedectomy (4C). For delivery to the semicircular canal a high postauricular incision is made and the superior semicircular canal is directly exposed (4D).

DETAILED DESCRIPTION AND PREFERRED EMBODIMENTS

Although preferred embodiments of the present invention are explained in detail, it is to be understood that other embodiments are possible. Accordingly, it is not intended that the invention is to be limited in its scope to the details of constructions and arrangement of components set forth in the following description or illustrated in the drawings. The invention is capable of other embodiments and of being practiced or carried out in various ways. Also, in describing the preferred embodiments, specific terminology will be resorted to for the sake of clarity. It is to be understood that each specific term includes all technical equivalents which operate in a similar manner to accomplish a similar purpose. Further, although the drawings are intended to illustrate the present invention, the drawings are not necessarily drawn to scale.

It has been shown that surgical trauma or manipulation of the inner ear, such as through cochlear implantation, can induce apoptosis in the hair cells of the inner ear and result in significant hearing loss.

It is believed that the hearing loss that results after trauma to the inner ear is due to apoptosis induced through caspases activation. Therefore, if one could inhibit the subsequent activation of caspases after surgical intervention, one could reduce or eliminate the loss of hearing that often accompanies such trauma.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol and ultraviolet radiation. Chemotherapeutic agents for treating cancer also are potent inducers of apoptosis.

At present and herein defined, the "caspase family" is known to comprise 12 members, caspases 1, 2, 3, 4, 5, 6, 7, 8, 9, 10, 11 and 12 (as reviewed by Cryns and Yuan, 1998, supra); one of these, caspase 9, is described as comprising the prototype caspase-recruitment domain (CARD), and thus the term "caspase" refers to any of caspases 1 through 12. See also U.S. Pat. Nos. 6,177,259 and 6,228,603 and herein incorporated into the specification as if set forth in their entireties.

Mammalian caspases are homologues of the product of the *C. elegans* cell-death gene ced-3 and have been shown to play important roles in regulating apoptosis (Cryns and Yuan, 1998, supra). A cowpox virus cytokine response modifier gene (crmA) encodes a serpin that is a specific inhibitor of two mammalian caspases, caspase-1 and caspase-8 (Zhou et al., 1997, J. Biol. Chem., 272: 7797-7800).

The caspases previously were referred to as the "Ice" proteases, based on their homology to the first identified member of the family, the interleukin-1β (IL-1β) converting enzyme (Ice), which converts the inactive 33 kiloDalton (kDa) form of IL-1β to the active 17.5 kDa form. The Ice protease was found to be homologous to the *Caenorhabditis elegans* ced-3 gene, which is involved in apoptosis during *C. elegans* development, and transfection experiments showed that expression of Ice in fibroblasts induced apoptosis in the cells.

A role for the caspases in apoptosis has been demonstrated by showing that overexpression of each of the identified caspases in various cell types results in apoptosis of the cell. In addition, expression in cells of CrmA, which is expressed by cowpox virus, was shown to protect the cells from undergoing cell death in response to various inducers of apoptosis by inhibiting caspase-1 activity. CrmA also was shown to bind caspase-3 and to inhibit proteolysis of the poly (ADP-ribose) polymerase (PARP) due to caspase-3, whereas a CrmA point mutant lacking the ability to bind caspase-3 did not inhibit proteolysis. PARP, as well as other cellular proteins including lamin B, topoisomerase I and β-actin, are degraded during apoptosis of a cell.

Caspase Inhibitors

Caspases have been shown to be inhibited by certain peptide fragments which presumably bind to the active site of the enzyme. The synthetic tetrapeptide VAD (Val-Ala-Asp) coupled to fluoromethylketone (VAD-fmk) or the N-benzyloxycarbonyl-derivative (zVAD-fmk) are synthetic permeable inhibitors of caspases (caspase-1) that have the same spectrum of activity as derivatives of YVAD (Tyr-Val-Ala-Asp). This tetrapeptide coupled to fluoromethylketone (YVAD-fmk) is a synthetic inhibitor of caspases. The aldehyde derivative (YVAD-CHO) is another inhibitor. The N-Acetyl-derivatives of these compounds (Ac-YVAD-AFC, Ac-YVAD-CHO) and the N-benzyloxycarbonyl-derivatives (indicated by the prefix z: ZYVAD-AFC, ZYVAD-AMC, zYYAD-fmk) as well as chloromethyl ketone derivatives (cmk; YVAD-CMK) are also used.

Another derivative (Ac-VAD-CMK; N-Acetyl-VAD-chloromethyl ketone derivative) is another inhibitor with a broad spectrum. zVAD-fmk has been shown also to inhibit efficiently cathepsin B activity in vitro and in tissue culture cells at concentrations used to demonstrate the involvement of caspases and thus appears to have non-specific effects.

Treatment of cells with caspase inhibitors can inhibit characteristic biochemical and morphological events associated with cell death by apoptosis. There are numerous references to these compounds in the literature. See Fernandes-Alnemri T., Cancer Research 55(24): 6045-6052 (1995); Fernandes-Alnemri T., PNAS (USA) 93(15): 7464-7469 (1996); Muzio M. et al., Cell 85(6): 817-827 (1996); Nicholson D W et al., Nature (London) 376(6535): 37-43 (1995); Rotonda J et al., Nat, Struct. Biol. 3(7): 619-625 (1996); Schotte P et al., FEBS Lett. 442(1): 117-121 (1999); Talanian R V et al., JBC 272 (15): 9677-9682 (1997).

It has also been found that caspases may be inhibited by another family of proteins called Inhibitors of Apoptosis proteins (IAP). Liston et al., Nature 379:349-353 (1996). Ambrosini et al., Nat. Med. 3:917-921 (1997); Bertin et al., J. Virology 70:6251-6259 (1996); Birnbaum et al., J. Virology 68:2521-2528 (1994); Roy et al., EMBO J. 16:6914-6925 (1997). X-linked inhibitory protein (XIAP), as well as the inhibitory proteins cIAP-1 and cIAP-2 block two distinct pathways of caspase activation by inhibiting different caspases, and are described in detail in U.S. Pat. No. 6,228,603 and herein incorporated by reference herein as if fully set forth in its entirety.

The baculovirus inhibitor of apoptosis protein repeat (BIR) is a domain of tandem repeats separated by a variable length linker that seems to confer cell death-preventing activity. Eight other genes (BIRC1, BIRC1.1, BIRC2, BIRC5, BIRC6.3, BIRC6.4, BIRC7, BIRC8) in the database also contain this motif. The BIR domain is found in proteins belonging to the IAP (inhibitor of apoptosis proteins) family.

Definitions

Biologically active agent" or "biologically active substance" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

As used herein, the terms, inject, administer, deliver are synonymous and mean the transfer of the composition being referred to from one reservoir or repository to a tissue, cell, or part of an organ, tissue, fluid or space.

The terms "therapeutic agent", "therapeutic composition", and "therapeutic substance" as well as "protein of interest" refer, without limitation, to any composition that can be used to the benefit of a mammalian species. Such agents may take the form of ions, small organic molecules, peptides, proteins or polypeptides, oligonucleotides, and oligosaccharides, for example. As defined herein, a therapeutic protein of interest can be any protein, protein fragment, peptide or peptide fragment that can be used to the benefit of a mammalian species.

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine).

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

Viral Vectors

A number of different gene therapy vectors have been tried in the inner ear. Adenoviral vectors are the best characterized because they are easy to produce and can carry a large amount of DNA. Several genes driven by different promoters can be transferred through this system. Although adenovirus is easy to use, but it has a limited expression time and has been associated with adverse immune reactions. Adeno-associated virus (AAV) is a smaller vector with more limited capacity that may allow long-term expression of transferred genes. It is more difficult to produce than adenovirus but has the advantage of not being associated with any known human disease. Herpes virus vectors have been used in a variety of applications and are capable of carrying large gene payloads. Theses vectors have the potential of maintaining long-term expression of the transferred gene and are particularly suited for targeting neurons. Liposomal or nonviral gene delivery uses charged lipids or polymers to condense the DNA to be transferred. Unfortunately at present liposomal delivery is less efficient than viral methods of gene transfer.

Adeno-Associated Viral Vectors

AAV is a parvovirus that carries an approximately 4500-bp genome flanked by terminal repeat sequences. These sequences are needed for the initiation of DNA replication and viral packaging. The native virus can exist in a lytic life cycle or can integrate into the host cell's DNA as a provirus. A helper virus (adenovirus) is needed for the virus to complete the lytic cycle or for production of an AAV vector. The existence of a latent state allows this vector potentially to be used for treatments that require long expression periods. The size of the genes that can be transferred using this system is limited by the overall size of the vector particle. About 95% of the AAV native genome can be replaced. It is not clear, however, whether the recombinant vectors that are produced truly integrate into the host genome. One of the great advantages of this packaging system is that it is not associated with any known human disease, making it a safe vector to use (Lalwani A. K., et al., Adv. Otorhinolaryngol., 2002;61:28-33). Recent developments in AAV vectorology include production of more concentrated vector stocks, which is particularly important for applications in the inner ear where a there are limitations on the volume of vector that can be delivered.

Herpes Simplex Vectors

Herpes simplex-derived vectors provide an ideal method for gene transfer to neurons. The most commonly used vector in this category is derived from herpes simplex type I (HSV 1). The native virus is able to infect both dividing and post-mitotic cells and has a broad tissue tropism. This virus also can assume a latent state in neuronal cells and exists as an episome in the nucleus of neurons. Problems relating to integration of the viral genome into the host's DNA are therefore not an issue. Generally cells infected with these viruses also escape immune surveillance. HSV 1 is a 152-kb double-stranded DNA virus coated in an envelope consisting of 12 glycoproteins. The genome contains more than 70 open reading frames. Because of the large size of the genome, vectors derived from HSV 1 can carry multiple large genes. During its natural life cycle, HSV 1 infects epithelial cells and fibroblasts in the skin and enters a lytic phase. The resulting released viruses fuse with local nerve fibers and through retrograde transport arrive at the neuronal cell body. A lytic cycle can then recur, or the virus can enter a latent stage in the nucleus of the neuron (Glorioso J. C. et al., Annu. Rev. Microbiol., 1995;49:675-710). During this stage only latency-associated RNAs are produced. Some vectors have been derived that take advantage of this virus's biology to link gene expression to latency promoters, thereby producing long-term stable gene expression in post-mitotic neurons. Replication-deficient vectors derived from HSV 1 have been produced by deleting ICP4, and growing vectors on a permissive cell line. Multiple generations of more advanced vectors have been produced by deleting additional early genes and growing the vector on engineered cell lines.

Retroviral Vectors

Retroviruses are RNA viruses and were the first viruses to be used for gene therapy. Their basic genetic structure allowed construction of a helper-free packaging system that carried the viral genes gag, pol, and env in trans. These vectors yield long-term expression of transferred genes but raise some potential concerns regarding insertional mutagenesis. Thus insertion of the pro-viral genome into the hosts DNA may cause mutations. These vectors are well characterized but have the disadvantage of being able to enter only dividing cells. Currently a new type of retroviral vector, lentiviral vectors, has been developed. These vectors are derived from HIV and simian immunodeficiency virus and are able to infect non-dividing cells. Lentiviral vectors are seen as having significant potential to provide long-term stable expression of transferred genes (Van De Water T. R., et al., Ann. NY Acad. Sci., 1999;884:345-60).

Adenoviral vectors are most commonly based on adenovirus serotype 5, a double-stranded DNA vector of 35 kilobase (kb) of which 30 kb can be replaced in current constructs. Early-generation vectors carry deletions of early genes E1 and E3, the function of which is supplied by engineered cell lines in trans. Adenovirus is a non-enveloped virus that attaches to cells by two main mechanisms. The fiber coat protein of the vector binds the coxsackie adenovirus receptor, and penton proteins bind cell-surface integrins. The vector then enters the cell through endocytosis and completes its life cycle as a non-integrating nuclear episome.

Newer-generation adenovectors include deletions of additional early genes, in particular, deleted of the E4 region. They have several advantages for use in the inner ear. E1/E3/E4-deleted vectors have been shown to be less cell disrupting in other delivery systems and hence less toxic following delivery to the inner ear. The E4 region of adenovirus encodes several proteins that modulate the host cell's function. In studies of primary endothelial cells, E1/E3/E4-deleted vectors have been shown to be less perturbing than adenovirus vectors containing E4 (Qian H. Set al., Circ. Res. 2001;88(9): 911-7; Rafii S. et al., Circ. Res. 2001;88(9):903-10; Ramalingam R., et al., J. Virol. 1999;73(12):10183-90. Studies in human embryonic lung fibroblasts have also suggested that E1/E3/E4 vectors reduce the risk of cell perturbation (Hobbs WE, et al., J. Virol. 2001;75(7):3391-403).

First generation replication-deficient adenoviral vectors of the present invention were constructed with the E1A, E1B and a portion of E3 were deleted from the viral genome, and the *E. coli* β-galactosidase gene (β-gal) was inserted under control of the Cytomegalovirus (CMV) promoter (U.S. Pat. Nos. 5,168,062 and 5,385,839) and designated AD.lacZ (Davidson et al., Nat. Genet. 1993; 3:219-223; Li et al., Ophthalmol. Vis. Sci. 1994; 35:2543-2549). Other promoters can be used, such as platelet-derived growth factor (PDGF), neuron-specific enolase (NSE), and elongation factor 1alpha (EF-1alpha), as well as mouse and human Cytomegalovirus and chicken β-actin (Luebke A. E., et al., Hum. Gene Ther., 2001; 12:773-781).

Newer-generation adenoviral vectors of the present invention were constructed similarly to the vectors above except that the E4 region was also deleted, along with other modifications that significantly lower the expression of viral genes in transduced cells, and which do not change cellular gene expression (Brough et al. J. Virol. 1996; 71:6496-6501; Ramalingam et al., Blood 1999; 93:2396-2944; Kanzaki et al., Hear. Res. 2002; 169:112-120). All references described in the specification are hereby incorporated by reference herein as if fully set forth in their entireties.

EXAMPLE 1

Round Window Approach

Adult CBA mice were anesthetized using intraperitoneal Avertin (2,2,2 Tribromoethanol, Sigma-Aldrich, T4,840-2). A dorsal postauricular incision was made and the bone medial to the tympanic ring was exposed. Using a No. 18 needle, a hole was drilled exposing the middle ear space medial to the tympanic ring. The round window niche and the bone overhanging the niche were both identified. The bone was scraped away revealing the round window membrane. The adenoviral vector with the E1/E3/E4 deletions expressing gfp driven by a CMV promoter was used (Ad11D) for all experiments (see Kanzaki et al. supra).

Vector injections consisted of $10^8$ i.p./μL of vector in 0.5-4.0 μL of volume (n=5 for each condition). Vector injections were carried out using a Hamilton microsyringe with 0.25 μL graduations. A 32-gauge needle was used to puncture the round window membrane using a micromanipulator (Singer Instruments, UK) while the animals were immobilized to minimize injection trauma. After the injection, the round window was patched with a small piece of muscle tissue.

For each approach, 3 control animals were injected with 1-4 μL of artificial perilymph to control for damage induced by hydraulic forces. A subset of animals were injected with a 1 μL volume of vector supplemented ($10^9$ to $10^{13}$ i.p./mL) with 2 μL of pancaspase inhibitor zVAD-FMK (1 mM) to test the effect of inhibiting apoptosis (n=3) during injection. Twenty four hours after vector delivery, hearing was tested by auditory brainstem response audiometry.

Figure 1:
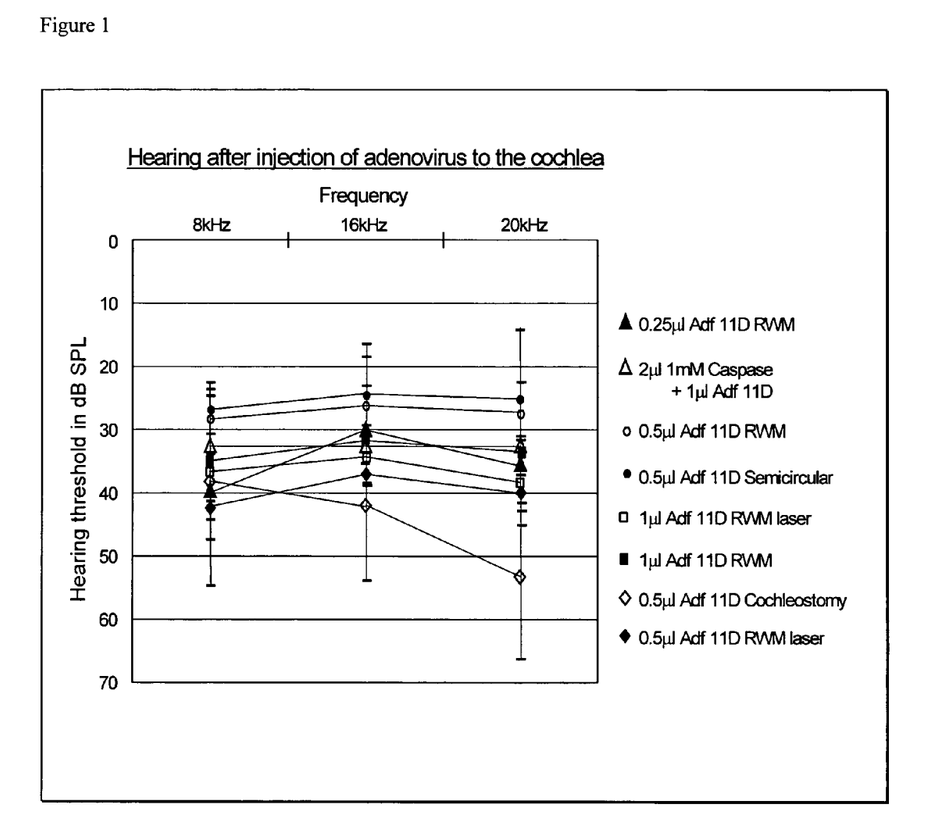
FIG. 1 is a summary graph depicting hearing in mice after injection of various volumes of adenovirus to the cochlea using different methods of injection.

Untreated mice had an average hearing threshold of 25 dB across all frequencies tested. Injection of 1-2 μl of artificial perilymph resulted in mild (10 decibel (dB)) hearing loss at all frequencies tested. Larger volumes (2-4 μl) of artificial perilymph resulted in significant (40-70 dB) hearing loss. Injections of greater than 1 μl Ad11D (about $10^{13}$ i.p./mL) also resulted in significant (40-70 dB) hearing loss. Lower doses of vector injected through the round window membrane resulted in minimal change in hearing with 1 μl volume causing 10 dB of hearing loss, and 0.5 μl of vector resulting in no hearing loss when compared to untreated controls (FIG. 1). Further, addition of a pancaspase inhibitor to the vector composition allowed injection volumes up to 3 μl with only minimal loss of hearing.

Figures 2A, 2F:
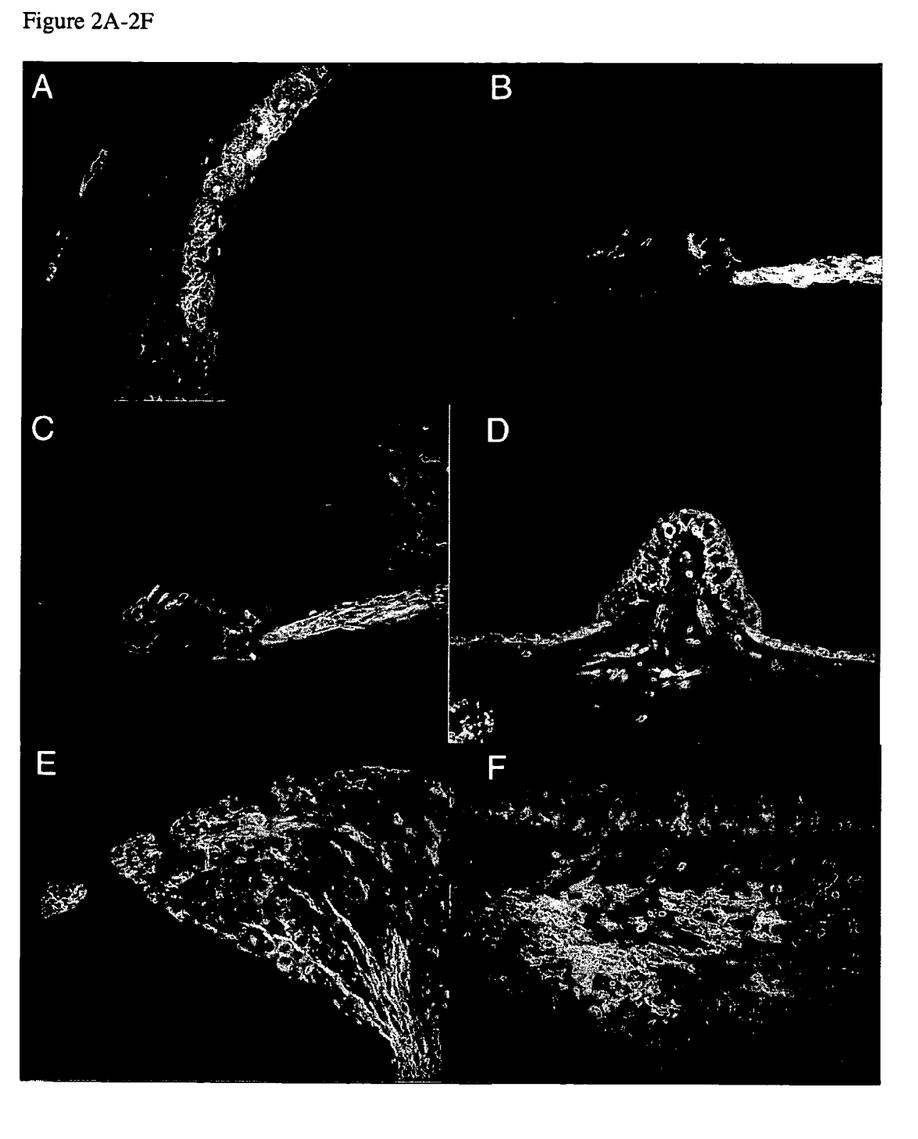
Figure 3A:
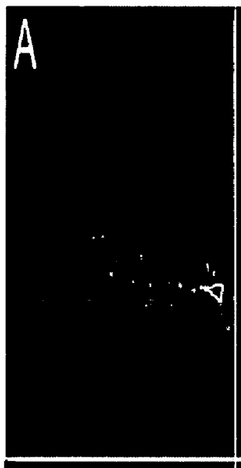
FIGS. 3A-3F are fluorescent micrographs showing mitochondrial function in hair cells. Cells with healthy and functioning mitochondria stain red and are depicted in 3D, 3E and 3F. The presence of hair cells are shown in green and depicted in 3A, 3B and 3C.
Figure 3B:
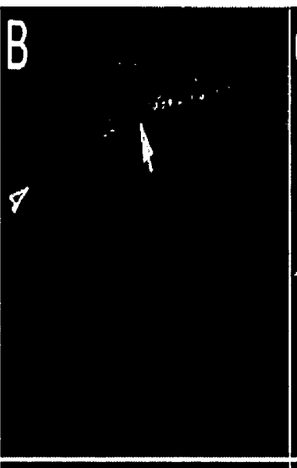
Figure 3C:
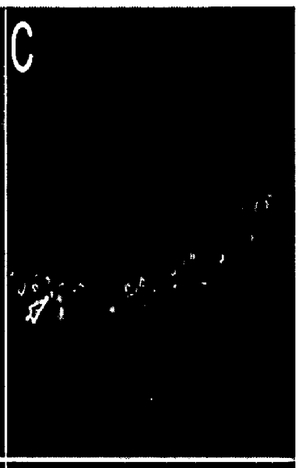
Figure 3D:
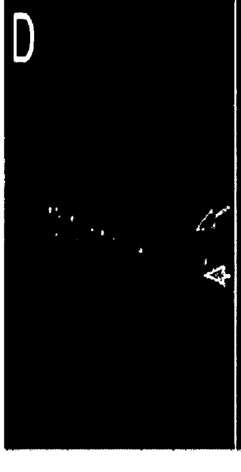
Figure 3E:
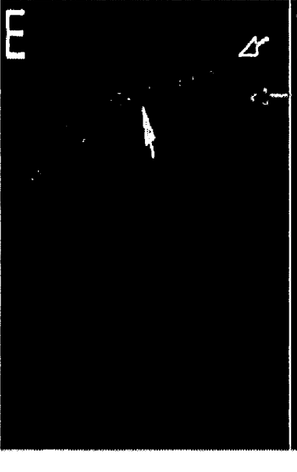
Figure 3F:
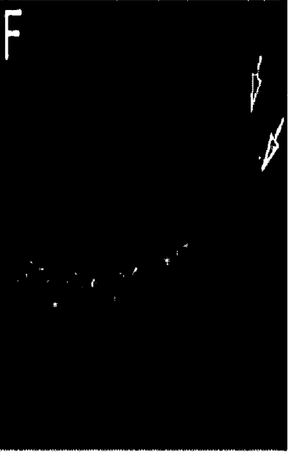
Figures 4A, 4D:
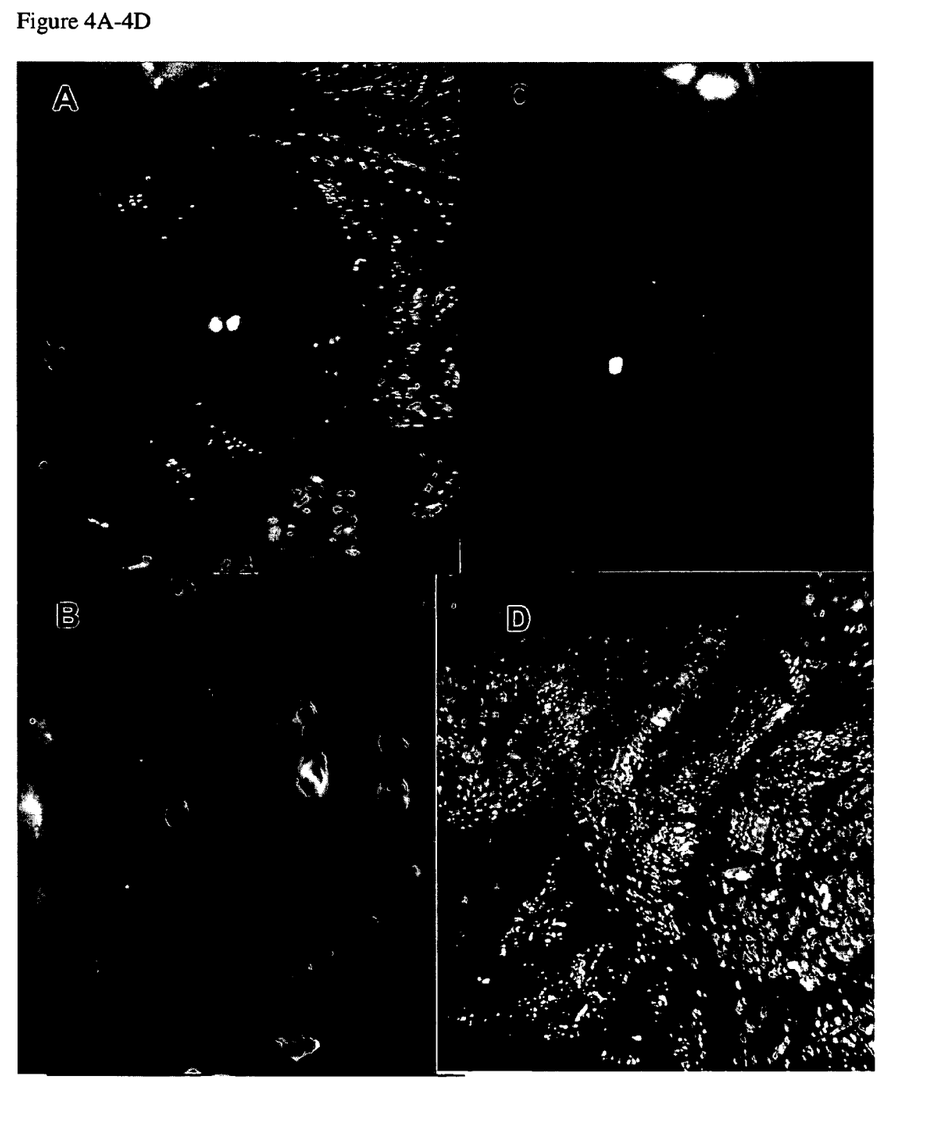
Figure 5:
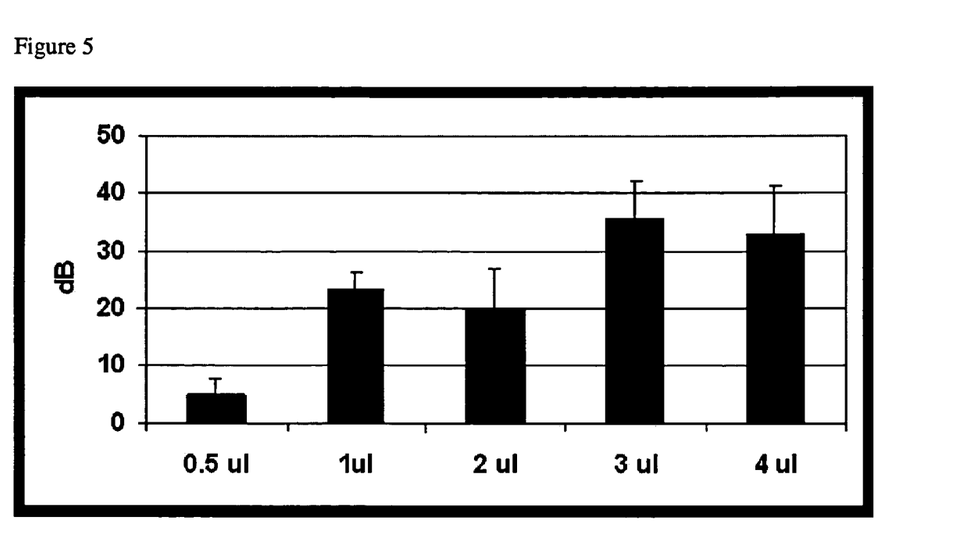
FIG. 5 shows the relationship between volume injected and change in hearing threshold in the mouse.
Figure 6:
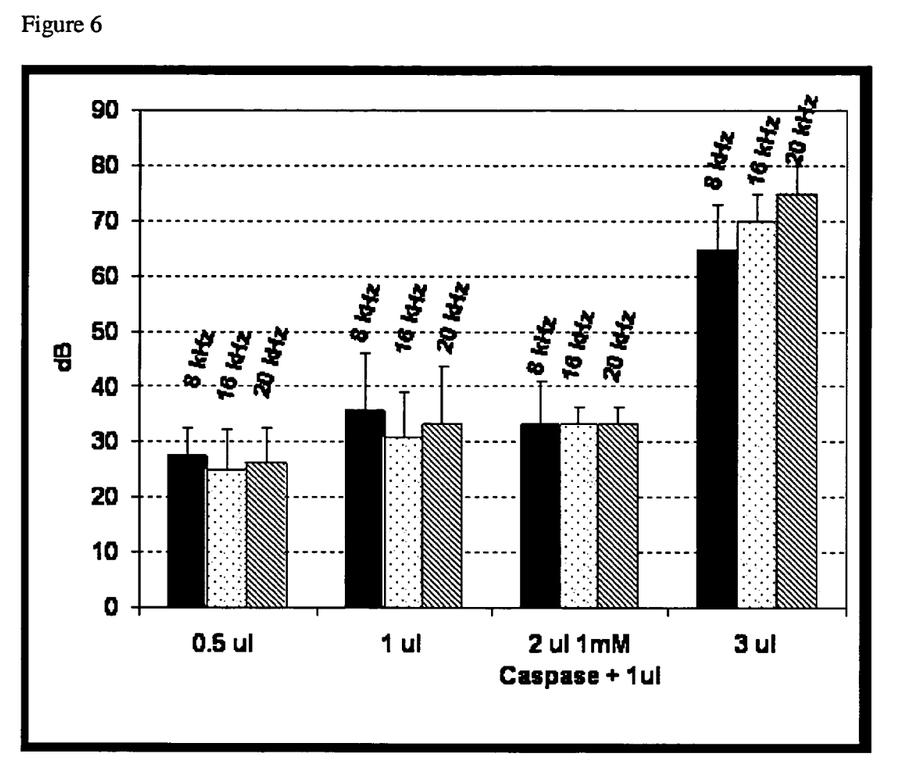
FIG. 6 shows the effect of a caspase inhibitor on hearing preservation.

The results demonstrated that successful expression of GFP was noted in the spiral ganglion, inner hair cells and occasional outer hair cells at all turns (FIG. 2).

EXAMPLE 2

Semicircular Canal Approach

After surgically exposing the temporal bone, the superior semicircular canal was identified and marked with India ink. An argon laser was used to create an opening in the bone with a single burst of 100 W/0.2 s. Injection of vector and data acquisition was carried out as described in Example 1. Injection of vector into the semicircular canal did not result in any hearing loss (FIG. 1).

EXAMPLE 3

Cochleostomy Approach

Animals were prepared as previously described in Example 1. The promontory overlying the basal turn of the cochlea was identified and marked with India ink. An argon laser was used to create a 200 μm cochleostomy just anterior to the round window using settings of 100 W/0.2 s. Injection of vector was then carried out as in Example 1. The cochleostomy was sealed with a piece of muscle tissue, and the animal was allowed to recover. Use of a basal turn cochleostomy with a low volume of vector injection (1 μL) having approximately $1 \times 10^{13}$ infectious particles per mL resulted in hearing loss at 20 kHz, suggesting that this approach is more damaging than direct injection through the round window membrane (FIG. 1).

EXAMPLE 4

Auditory Brainstem Response Collection

Auditory brainstem responses (ABR) were elicited using a Tucker Davis System 3 apparatus. Mice were anesthetized and maintained on a heating pad. Needle electrodes were placed on the ipsilateral mastoid tip and at the vertex. Precalibrated stimuli ranging from 500 to 24,000 Hz were then presented from 90 to 10 dB in 5 dB steps. An average of 1,000 stimuli was collected. The data were stored and graphically rendered using Excel™.

EXAMPLE 5

Drug Delivery in Humans via Stapedial Puncture

The procedure can be carried out under general or local anesthesia. The ear canal is washed with a betadine solution and allowed to dry. Sterile drapes are applied per surgeon preference. The ear canal is visualized with an operating microscope and the vascular strip is injected with 1 cc of 1% lidocaine plus 1/100,000 epinephrine. An incision is made parallel to the annulus and the tympanic membrane is elevated. The chorda tympani nerve is identified and preserved. If necessary, the scutum is partially removed by curettage until the stapes is seen. The microscope is positioned to visualize the stapes footplate. Using an Argon or $CO_2$ laser, a single hole is drilled into the center of the stapes footplate allowing free flow of perilymph. A microsyringe with a 30# needle is prepared with the drug that is to be delivered. Using a micromanipulator the needle is inserted into the hole that has been created in the footplate and the sample is slowly injected by hand or injected mechanically. Estimated tolerated volumes are 1-2 μL. The footplate hole is then sealed with a small piece of fat from the earlobe which was previously harvested (FIG. 4A-4D).

The ability to model this approach in rodents has been limited due to the presence of an artery that crosses the stapes footplate (the stapedial artery). By using a laser the inventors are able to create a hole in the edge of the stapes footplate of a mouse (FIG. 4B). Adf (adenovector carrying the gfp gene) was then injected into the vestibule of the mouse. A total of 0.25-3 μL were injected using a micromanipulator and microsyringe. After recovery, hearing was measured as in the previous examples and there was no significant hearing loss observed. Distribution of GFP activity was seen in the spiral ganglion, vestibular ganglion and isolated sections of the sensory epithelium, demonstrating that this approach is effective in an animal model (FIG. 2A-2F).

Use of this stapedetomy technique is extremely safe in humans. Rather than placing a prosthesis, a known volume of drug can be infused into the vestibule (perilymph space) via this approach. This is particularly useful for delivering single bolus of large molecules such as proteins, nucleic acids and gene therapy vectors. Moreover, use of this technique with volumes of up to 10% of the total cochlear volume results in little or no damage to the inner ear and does not need the addition of caspase inhibitors to prevent damage.

EXAMPLE 6

Injection of Ad bcl2

The ear is prepared as in example 5. A hole is drilled into the stapedial footplate and between 0.5 μL-3.0 μL of a solution of adenovector encoding for the bc12 protein at approximately $10^9$ to $10^{13}$ i.p./mL is injected. Distribution of bc12 expression was seen in the spiral ganglion, vestibular ganglion and isolated sections of the sensory epithelium, demonstrating that this approach is effective in an animal model.

EXAMPLE 7

Cochlear Implantation

The ear is prepared as in example 5. A hole is drilled into the stapedial footplate and between 0.5 μL-3.0 μL of a solution of a caspase inhibitor in a concentration range of about 0.1-10 mM, is injected. The inhibitor can be VAD-fmk or zVAD-fmk or YVAD-fmk. The administration can be simultaneous with treatment or the can be prior to the treatment. After administration of the drug to the cochlea, implantation of the electrodes can be performed.

EXAMPLE 8

Traumatic Surgical Intervention

For patients with tumors of the cerebellopontine angle, aneurysms in the Circle of Willis or other tumors located at the base of the cranial vault, neuromas of the ear or others, there are little other routes of entry available to surgeons to treat these conditions other than entry underneath or proximal to the ear canal, which can result in significant hearing loss. In particular this would include approaches in which the semicircular canals are removed. Also amenable to this treatment are procedures where there is potential of vasospasm of the inner ear blood supply. Administration of a caspases inhibitor prior to such surgery would preserve hearing in these patients. For example, a patient would be prepared as in Examples 1 or 5 above and then between 0.5 μL-3.0 μL of a solution of a caspase inhibitor is injected. The remaining surgery would then be performed and the patient sent to recover.

EXAMPLE 9

Inhibition of Hearing Loss via Transfection of a IAP in the Inner Ear

The ear is prepared as in the examples above. A hole is drilled and between 0.5 μL-3.0 μL of a solution of Ad11d which encodes for X-linked inhibitory protein (XIAP) which inhibits many caspases along with GFP is injected into the inner ear. Transfection of XIAP causes diminution of the apoptosis and loss of hearing associated with the trauma to the ear and can allow surgical intervention days after the initial transfection, as the transfected hair cells will be producing XIAP.

EXAMPLE 10

Regeneration of Hearing and Balance

Many deafness genes exist, but the most common cause of hearing loss in American and European populations is a mutation in the connexin 26 (Cx26) gene. Cx26 has a carrier rate of 3%, similar to that for cystic fibrosis, and it causes about 20% of childhood deafness.

Mutations in Cx26 cause congenital syndromic and non-syndromic deafness—that is, the deafness is not accompanied by other symptoms, such as blindness. Cx26 is located on chromosome 13q11-12 and codes for a gap junction protein called connexin 26. Gap junctions are plasma membrane channels that allow the movement of small molecules and ions between adjacent cells. Gap junctions of the inner ear may play a role in maintaining potassium homeostasis, which is important for inner-ear function and, thus, hearing. It has been proposed that mutations in Cx26 may disrupt potassium circulation and result in deafness. See, Feldmann D., et al., Am. J. Med. Genet. 2004; 15;127A(3):263-7; Thomas T. et al., J. Biol. Chem. 2004;279(18):19157-68.

The ear is prepared as in example 5 above. A hole is drilled in the stapedial footplate and between 0.5 μL-3.0 μL of a solution of Ad11d which encodes for connexin 26 under control of a lentiviral promoter is injected. Transduction of the connexin 26 gene in the cells of the inner ear will restore function.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

The invention claimed is:

1. A method for delivering a pharmaceutical composition to the inner ear of a mammal without damaging hearing comprising the steps of:
   a) visualizing the ear canal;
   b) making an incision parallel to the annulus and elevating the tympanic membrane;
   c) preserving and identifying the chorda tympani nerve;
   d) visualizing the stapes footplate in the ear;
   e) drilling a hole in the center of the stapes footplate with a diameter sufficiently large to allow the flow of perilymphatic fluid;
   f) injecting about 0.25 μL-10.0 μL of a pharmaceutical composition for treatment of the inner ear of a mammal; and
   g) filling the hole in the stapes footplate.

2. The method of claim 1, wherein said pharmaceutical composition comprises an effective amount of adenoviral vector comprising a polynucleotide encoding for an anti-apoptotic polypeptide and a pancaspase inhibitor.

3. The method of claim 2, wherein said adenoviral vector has E1/E3/E4 deletions.

4. The method of claim 2, wherein said adenoviral vector comprises a promoter that regulates expression of said anti-apoptotic polypeptide.

* * * * *